United States Patent

[19]

Amselem

[11] 3,995,050
[45] Nov. 30, 1976

[54] AMINO-2 IMIDAZOLES
[75] Inventor: Armand Amselem, Toulouse, France
[73] Assignee: PARCOR, Paris, France
[22] Filed: Apr. 15, 1975
[21] Appl. No.: 568,362

[30] Foreign Application Priority Data
Apr. 30, 1974 France .............................. 74.14986

[52] U.S. Cl. .......................... 424/273; 260/247.5 E; 260/268 H; 260/293.7; 260/295 S; 260/295.5 S; 260/309; 424/248; 424/250; 424/266; 424/267
[51] Int. Cl.² ................ C07D 401/04; C07D 403/04
[58] Field of Search ........................ 260/309, 293.7; 424/273, 267

[56] References Cited
UNITED STATES PATENTS
3,459,763    8/1969    Gruenfeld ........................... 260/309

OTHER PUBLICATIONS
Burmistrov et al. Chem. Abst. 1965, vol. 62, column 14657.
Hiltmann et al. Chem. Abst. 1973, vol. 78, No. 136,283n.
Hiltmann et al. Chem. Abst. 1973, vol. 78, No. 136,299x.

*Primary Examiner*—Natalie Trousof
*Attorney, Agent, or Firm*—Cushman, Darby & Cushman

[57] ABSTRACT

Aminoimidazoles of the formula

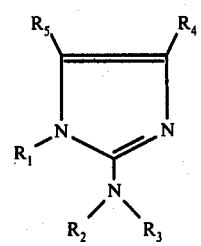

wherein $R_1$ is optionally substituted phenyl, $R_4$ is hydrogen or alkyl, $R_5$ is hydrogen or methyl and $R_2$ and $R_3$ form, together with the nitrogen atom to which they are bonded, a saturated heterocycle having 4 to 8 ring members, have valuable psychostimulant properties.

4 Claims, No Drawings

AMINO-2 IMIDAZOLES

The present invention relates to new imidazole derivatives, a process for preparing them, and their use, particularly in human and veterinary medicine.

The 2-amino imidazoles of the invention correspond to formula:

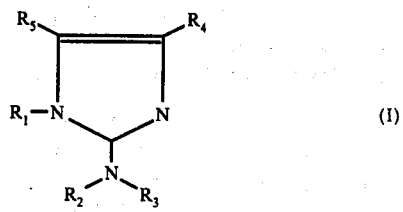

wherein $R_1$ is alkyl, alkenyl, alkynyl, cycloalkyl, phenylalkyl or phenyl, optionally mono- or poly-substituted by a halogen, alkyl, alkoxy, dialkylamino, alkoxycarbonyl, alkylthio, trifluoromethyl, nitro or cyano substituent, $R_4$ is hydrogen, halogen or alkyl, $R_5$ is hydrogen or methyl, $R_2$ and $R_3$ form, together with the nitrogen atom to which they are bonded, a saturated heterocycle with 4 to 8 ring-members, optionally incorporating a second oxygen or nitrogen heteroatom, which may carry an alkoxy, alkyl, alkylphenyl or halogen, or else $R_2$ and $R_3$ are both, independently of each other, hydrogen, or an alkyl, alkenyl, alkynyl, acyl, cycloalkyl, phenyl, benzyl or benzoyl radical, optionally mono- or poly-substituted by a halogen, alkyl, alkoxy, dialkylamino, alkoxycarbonyl, alkyl-thio, trifluoromethyl, nitro, cyano or oxo, while $R_3$ is not hydrogen, methyl or ethyl when both the following conditions are satisfied: $R_2$ is hydrogen, $R_1$ is hydrogen or phenyl, optionally mono- or disubstituted by a halogen, a lower alkyl, lower alkoxy or trifluoromethyl.

Compounds wherein $R_2$ and $R_3$ form a heterocycle, and those wherein at least one of $R_2$ and $R_3$ is acyl, particularly alkanoyl, phenyl, benzyl or benzoyl, optionally substituted, are preferred.

Advantageously, the alkyl radicals of the substituents are straight-chained or branched lower radicals having 1 to 12, preferably 1 to 6 carbon atoms. In particular, these radicals have up to 4 carbon atoms. The cycloalkyl radicals advantageously have 5 to 10, preferably 6 to 8 carbon atoms. When they are monosubstituted, the phenyl nuclei are advantageously substituted in the p-position relative to their point of attachment to the imidazole ring or the nitrogen atom in the 2 position of this ring, whereas disubstitution is generally at the two ortho positions. The acyl radicals are lower radicals, in particular alkanoyl. The preferred halogens are chlorine and bromine.

Interesting properties are obtained particularly when $R_1$ is hydrogen, methyl, ethyl, propyl, butyl, phenyl, methoxyphenyl, chlorophenyl, nitrophenyl, benzyl, phenethyl, cyclohexyl, propargyl or allyl, $R_2$ is methyl, ethyl, phenyl, benzyl, acetyl, benzoyl, cyclohexyl or chlorophenyl, or $R_2$ and $R_3$ form, with the nitrogen atom to which they are bonded, a pyrrolidino, morpholino, piperazino, tolylpiperazino, piperidino or azetidino ring.

The derivatives of the invention may be in the form of their acid addition salts. Among the pharmaceutically acceptable salts, are the addition salts with mineral acids, such as halohydric acids, particularly hydrochloric and hydrobromic acid, nitric acid, sulphuric acid, phosphoric acids, etc., or with organic carboxylic acids such as acetic acid, propionic acid, glycolic acid, malonic acid, succinic acid, maleic and hydroxymaleic acid, fumaric acid, malic acid, tartaric acid, citric acid, glucuronic acid, benzoic acid, mandelic acid, salicyclic acid and 4-amino-salicyclic acid, 2-phenoxy-benzoic acid, 2-acetoxy-benzoic acid, pamoic acid, nicotinic acid, isonicotinic acid, etc., or with organic sulphonic acids, such as methane sulphonic acid, ethanesulphonic acid, 2-hydroxy-ethanesulphonic acid, ethane 1,2-disulphonic acid, p-tolutenesulphonic acid, naphthalene 2-sulphonic acid, etc.

The derivatives of the invention may be in the form of quaternary ammonium compounds, using esters of alcohols and of strong organic or mineral acids, such as lower alkyl and/or lower phenylalkyl halides, sulphates or sulphonates of quaternary ammonium, for example methyl, ethyl, normal propyl, isopropyl or normal butyl chloride, bromide or iodide, etc., benzyl, phenethyl or 2-phenylethyl chloride, bromide or iodide, and dialkylsulphates in which the alkyl component is a lower alkyl, for example dimethyl sulphate, diethyl sulphate, etc., or the lower alkyl sulphonates, for example methylmethane sulphonate or ethyl-methane sulphonate, ethane sulphonate or toluene sulphonate, etc.

The invention also relates to a process for preparing the 2-amino imidazoles defined hereinbefore, which consists of reacting a reagent of formula:

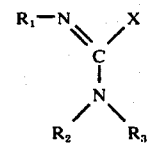

wherein X is halogen, mercapto, arylthio, alkoxy or aryloxy, with an amine of formula:

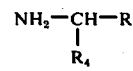

wherein R is ethynyl (—C≡CH) or dialkoxy-methyl, to obtain the intermediate product

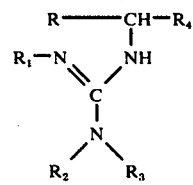

which cyclizes, spontaneously when R is ethynyl, but in the presence of a Lewis acid when R is dialkoxymethyl, to form a 2-amino imidazole wherein $R_5$ is methyl or hydrogen respectively, $R_1$ to $R_4$ have the meanings indicated hereinbefore and, when this imidazole is not substituted in the 2 or 4 position, whereas the desired imidazole is substituted in the 2 or 4 position, reacting the unsubstituted 2-amino-imidazole with a substitution reagent of formula $YR_2$ or $YR_4$, wherein Y is an electronegative monovalent radical, such as a halogen, to obtain the 2-amino-imidazole which has the substituent $R_2$ or $R_4$.

The first step of the process of the invention consists of reacting a reagent of formula:

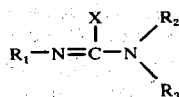

wherein $R_1$, $R_2$ and $R_3$ have the above-mentioned meanings, and X may represent a halogen (chloroformamidine), an —SH group (thiourea), an —S-alkyl or S-benzyl group (S-substituted isothiourea) or an O-alkyl group (O-substituted isourea), with optionally substituted propargylamine

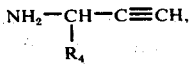

if it is desired that $R_5$ represent a methyl radical; or with an optionally substituted dialkylacetal-aminoacetaldehyde of formula

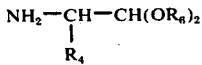

wherein $R_4$ has the above-mentioned meaning and $R_6$ represents a lower alkyl radical, if it is desired that $R_5$ should represent hydrogen.

The reaction is performed at elevated temperature, under refluxing, preferably at a temperature between 50° and 150° C, in the presence of a solvent the boiling temperature of which is between 50° and 150° C, for example an aromatic hydrocarbon, such as benzene, toluene, xylene, an alkanol, such as methanol, ethanol, propanol, isobutanol, dioxan, pyridine, etc.

The reaction is performed over a period of 2 to 30 hours. The use of a catalyst is not essential, although its presence in the medium does promote and accelerate the reactions. Advantageously, p-toluene sulphonic acid or a propargylamine salt or a tertiary amine salt is used as catalyst.

Whereas cyclization is spontaneous and total in the reaction with propargylamine, it is effected in 2 stages when acetal is used: cyclization of the intermediate derivative is effected by refluxing with 2N HCl.

The dialkyl acetal of aminoacetaldehyde used is, for example, the dimethylated or diethylated derivative, which are the two most commonly used in organic synthesis.

Purification of the products obtained by the process of the invention is preferably performed by extracting with an organic solvent such as methylene chloride, evaporating the solvent and recrystallizing from a solvent such as isopropanol.

The starting compounds of formula II can be used in the form of salts, such as hydriodides, hydrochlorides, hydrobromides or sulphates, for example.

As regards the substituents $R_1$ and $R_5$, they are determined as they appear in the starting materials. As for the other substituents $R_2$, $R_3$ and $R_4$, if they do not appear in the intermediate synthesis products, they may be added to the molecule by reaction, after cyclization of the imidazole nucleus.

Thus, when the radical $R_2$ or $R_3$ represents hydrogen in the derivative of formula IV or VI, the —$NHR_2$ or $NHR_3$ group may easily be alkylated, acylated, converted into urea, etc.

The same applies to the $R_4$ radical which, when it represents a hydrogen atom, may readily be replaced by a halogen, particularly chlorine or bromine, according to known methods.

The quaternary ammonium salts and derivatives of the compounds of formula I are prepared by methods which are well-known to specialists.

The following non-restrictive examples are given as an illustration of the preparation of the compounds according to the invention.

EXAMPLE 1

Preparation of 5-methyl-1-phenyl-2-phenylamino imidazole (derivative No. 1) $R_1=R_2=$phenyl; $R_3=R_4=$H; $R_5=$methyl.

A mixture of 37 g (0.153 mol) of N,N'-diphenyl-S-methyl isothiourea, 25.2 g (0.46 mol) of propargylamine, 0.3 g of p-toluenesulphonic acid and 150 ml of butanol is refluxed for 20 hours. After the solvent has been evaporated in vacuo, the residue is taken up in methylene chloride and the solution obtained is washed with water. The organic phase is separated, dried on sodium sulphate and filtered. After evaporation of the solvent, the residue is recrystallized from isopropanol. 33 g of white crystals are obtained. (Yield 87%) Melting point 91° C, determined by the Koefler block.

EXAMPLE 2

Preparation of 2-anilino-4,5-dimethyl-1-phenyl imidazole (derivative No. 2); $R_1=$phenyl; $NR_2R_3=$anilino; $R_4=R_5=$methyl.

Using the same method, but replacing 25.2 g of propargylamine (0.46 mol) with 31.7 g (0.46 mol) of 2-amino-3-butyne, crystals are obtained (yield 85%), melting point 105° C measured by the Koefler block.

EXAMPLE 3

Preparation of 1-methyl-3-phenyl-3-(5-methyl-1-phenyl-2-imidazolyl) urea (derivative No. 3, $R_1=R_3=$phenyl; $R_2=R_4=$H; $R_5=$methyl).

A mixture of 6.25 g (0.025 mol) of 5-methyl-1-phenyl-2-phenylamino imidazole (derivative No. 1), 1.44 g of methyl isocyanate (0.025 mol) and 20 ml of benzene are refluxed for 6 hours. After the solvent has been evaporated in vacuo, the residue is taken up in ether, filtered, and recrystallized from a mixture of isopropanol/isopropyl ether. 4.55 g of greyish-beige crystals are obtained in a yield of 59.5%, melting point 147° C measured by Koefler's block.

EXAMPLE 4

Preparation of 2-anilino-1-phenyl imidazole (derivative No. 4) $R_1=R_2=$phenyl, $R_3=R_4=R_5=$H.

A mixture of 18 g (0.075 mol) of N,N'-diphenyl-S-methyl isothiourea, 16.65 g (0.150 mol) of dimethyl aminoacetaldehyde acetal, 0.3 g of p-toluene-sulphonic acid and 100 ml of butanol is refluxed for 30 hours.

After the solvent has been evaporated in vacuo, the residue is taken up in ether and filtered. The solution is washed with water; the organic phase is separated and dried on sodium sulphate. By evaporation of the ether, the intermediate guanidine is obtained, which is refluxed for 2 hours in 75 ml of 2N hydrochloric acid.

After cooling, the solution is made alkaline with a dilute sodium hydroxide solution and extracted with methylene chloride.

The combined organic phases are then washed with water, dried on sodium sulphate and evaporated. The residue obtained is recrystallized from isopropanol. White crystals are obtained in a yield of 57%, melting point 135°–136° C, measured by the Koefler block.

EXAMPLE 5

Preparation of 2-anilino-1,4-diphenyl-imidazole (derivative No. 5) $R_1=R_2=R_4=$phenyl; $R_3=R_5=$H.

Using the same method, but replacing the aminoacetaldehyde dimethylacetal (0.15 mol) with 31.35 g (0.15 mol) of 1-amino-1-phenylacetaldehyde diethylacetal, white crystals are obtained (yield 62%), melting point 126° C, determined by the Koefler block.

EXAMPLE 6

Preparation of 5-methyl-1-phenyl-2-pyrrolidino-imidazole (derivative No. 6); $R_1=$phenyl, $NR_2R_3=$pyrrolidino, $R_4=$H; $R_5=$methyl.

A mixture of 10 g (0.046 mol) of N-phenyl-N′-tetramethylene S-methyl isothiourea, 7.6 g (0.140 mol) of propargylamine, 0.3 g of p-toluenesulphonic acid and 75 ml of butanol is refluxed for 2 hours. After evaporation of the solvent, the residue is taken up in methylene chloride and filtered. The solution is washed with water, dried on sodium sulphate and filtered. The residue, after evaporation of the solvent, is recrystallized from isopropyl ether. 5.65 g (yield 54%) of white crystals are obtained, melting point 110° C, determined by the Koefler block.

The same product was also prepared according to the following method: A mixture of 205 g of N-phenyl N′-tetramethylene S-methyl isothiourea hydriodide (0.59 mol) and 119 g of propargyl-amine (1.17 mol), dissolved in 1500 ml of pyridine, is heated to 105° C for 1 hour.

After evaporation of the solvent, the residue is taken up in methylene chloride and treated as in the preceding example. (Yield 87%)

EXAMPLE 7

Preparation of 1-phenyl-2-pyrrolidino-imidazole (derivative No. 7) $R_1=$phenyl; $NR_2R_3=$pyrrolidino; $R_4=R_5=$H.

A mixture of 20 g (0.058 mol) of N-phenyl-N-tetramethylene S-methyl isothiourea, 12.2 g (0.116 mol) of aminoacetaldehyde dimethylacetal and 75 ml. of pyridine is heated to 100° C for 7 hours.

After evaporation of the solvent, the residue is taken up in methylene chloride and filtered. The solution is washed with water, dried on sodium sulphate and concentrated in vacuo. The residual oil consisting of the intermediate guanidine is dissolved in 75 ml of 2N hydrochloric acid, and the solution obtained is heated to boiling for 1 hour.

After cooling, the medium is made alkaline by adding dilute sodium hydroxide solution, then extracted with methylene chloride.

The organic phases are combined, washed with water, dried on sodium sulphate, filtered, and evaporated. The oil obtained consists of the desired product, which is isolated in the form of the fumarate, by adding a fumaric acid solution. The salt is then recrystallized from isopropanol.

White crystals are obtained (yield 55%), melting point 169° C, measured by the Koefler block.

EXAMPLE 8

Preparation of 2-(N-acetylanilino)-1-phenyl imidazole (derivative No. 8) $R_1=R_2=$phenyl; $R_3=$acetyl; $R_4=R_5=$H.

15 ml of acetic anhydride are added to a solution of 7.7 g (0.33 mol) of 1-phenyl-1-phenylamino imidazole (derivative No. 2) in 40 ml of pyridine.

The mixture is heated to 80° for 16 hours, then cooled and poured onto ice. After extracting with methylene chloride, the organic solution is washed with water, dried on sodium sulphate, then evaporated. By recrystallization from isopropanol, beige crystals are obtained (yield 57%), melting point 122° C, measured by the Koefler block.

EXAMPLE 9

Preparation of 2-(N-acetylanilino)-1-phenyl-5-methyl imidazole (derivative No. 9); $R_1=R_2=$phenyl; $R_3=$acetyl; $R_4=$H; $R_5=$methyl.

This product, like the preceding one, was prepared, by the same method, by acetylating S-methyl-1-phenyl-2-phenylamino imidazole (derivative No. 1): it occurs in the form of beige crystals (yield 69%), melting point 109° C, determined by the Koefler block.

EXAMPLE 10

Preparation of 2-anilino-4-bromo-5-methyl-1-phenyl imidazole (derivative No. 10); $R_1=R_2=$phenyl; $R_3=$H; $R_4=$bromo; $R_5=$methyl.

To a solution of 10 g (0.344 mol) of the acetylated derivative No. 9, 2-(N-acetylanilino)-1-phenyl-5-methyl imidazole in 100 ml of chloroform, are added, at normal temperature, 5.5 g (0.344 mol) of bromine dissolved in 30 ml of chloroform. The mixture is left to stand for 12 hours, then washed with a dilute sodium carbonate solution. The organic solution is then washed with water, dried on sodium sulphate and evaporated.

The residue is taken up in 100 ml of ethanol and 15 ml of a 5% NaOH solution. The mixture is refluxed for 15 minutes. Then the ethanol is removed by evaporation and the aqueous solution is extracted with methylene chloride. The combined extracts are washed with water. The organic solution is dried on sodium sulphate and evaporated. The solid residue is recrystallized from isopropyl ether. Yellowish crystals are obtained (yield 46%), melting point 150° C, measured by the Koefler block.

The following compounds were prepared by analogous processes:

Derivative 11: 2-morpholino-1-phenyl imidazole (m.p. 91° C) $R_1=$phenyl, $NR_2R_3=$morpholino; $R_4=R_5=$H.

Derivative 12: 1-benzyl-5-methyl-2-pyrrolidino imidazole, fumarate (m.p. 147° C) $R_1=$benzyl, $NR_2R_3=$pyrrolidine, $R_4=$H; $R_5=$methyl.

Derivative 13: 1-phenyl-2-piperidino imidazole (m.p. 79° C), $R_1=$phenyl, $NR_2R_3=$piperidino, $R_4R_5=$H.

Derivative 14: 5-methyl-2-morpholino-1-phenyl imidazole, oxalate (m.p. 160° C); $R_1=$phenyl, $NR_2R_3=$morpholino; $R_4=$H; $R_5=$methyl.

Derivative 15: 5-methyl-2-dimethylamino-1-phenyl imidazole (m.p. 85° C) $R_1$=phenyl, $R_2$=$R_3$=$R_5$=methyl; $R_4$=H.

Derivative 16: 1-cyclohexyl-2-cyclohexylamino imidazole (m.p. 188° C) $R_1$=$R_2$=cyclohexyl; $R_3$=$R_4$=$R_5$=H.

Derivative 17: 2-p-methoxyanilino-1-p-methoxy-phenyl imidazole (m.p. 102° C) $R_1$=$R_2$=p-methoxy-phenyl, $R_3$=$R_4$=$R_5$=H.

Derivative 18: 2-p-methoxy-anilino-1-p-methoxy-phenyl-5-methyl imidazole (m.p. 123° C) $R_1$=$R_2$=p-methoxyphenyl, $R_3$=$R_4$=H, $R_5$=methyl.

Derivative 19: 2-(4-chloro-anilino)-1-(4-chloro-phenyl)-5-methyl imidazole (m.p. 183° C) $R_1$=$R_2$=p-chloro-phenyl; $R_3$=$R_4$=H; $R_5$=methyl.

Derivative 20: 2-(4-chloro-anilino)-1-(4-chloro-phenyl) imidazole (m.p. 161° C) $R_1$=$R_2$=p-chloro-phenyl; $R_3$=$R_4$=$R_5$=H.

Derivative 21: 5-methyl-2-piperidino-1-phenyl imidazole (m.p. 154° C) $R_1$=phenyl; $NR_2R_3$=piperidino; $R_4$=H; $R_5$=methyl.

Derivative 22: 1-p-chlorophenyl 5-methyl-2-pyrrolidino imidazole (m.p. 158° C) $R_1$=p-chloro-phenyl; $NR_2R_3$=pyrrolidino; $R_4$=H; $R_5$=methyl.

Derivative 23: 2-diethylamino-5-methyl-1-phenyl imidazole (m.p. 112° C) $R_1$=phenyl; $R_2$=$R_3$=ethyl; $R_4$=H; $R_5$=methyl.

Derivative 24: 1-butyl-2-(N-methyl-anilino) imidazole (m.p. 129°–130° C) $R_1$=butyl; $R_2$=phenyl; $R_3$=methyl; $R_4$=$R_5$=H.

Derivative 25: 5-methyl-2-(N-methylanilino) 1-phenyl imidazole (m.p. 100° C) $R_1$=$R_2$=phenyl; $R_3$=$R_5$=methyl, $R_4$=H.

Derivative 26: (N-2-methylanilino)-1-phenyl imidazole (m.p. 135° C) $R_1$=$R_2$=phenyl; $R_3$=methyl; $R_4$=$R_5$=H.

Derivative 27: 1-methyl-2-(N-methylanilino imidazole (m.p. > 260° C) $R_1$=$R_2$=methyl; $R_3$=phenyl; $R_4$=$R_5$=H.

Derivative 28: 1,5-dimethyl-2-(N-methylanilino) imidazole (m.p. 133° C) $R_1$=$R_2$=$R_5$=methyl; $R_3$=phenyl; $R_4$=H.

Derivative 29: 1-(2-chloro-phenyl)-5-methyl-2-pyrrolidino imidazole (m.p. 160° C); $R_1$=2-chloro-phenyl, $NR_2R_3$=pyrrolidino; $R_4$=H; $R_5$=methyl.

Derivative 30: 2-(N-acetyl p-chloroanilino)-1-p-chlorophenyl 5-methyl imidazole (m.p. 116°–118° C) $R_1$= $R_2$=p-chlorophenyl, $R_3$=acetyl; $R_4$=H; $R_5$=methyl.

Derivative 31: 5-methyl-1-p-nitrophenyl-2-pyrrolidino imidazole (m.p. 150° C) $R_1$=p-nitrophenyl, $NR_2R_3$=pyrrolidino; $R_4$=H; $R_5$=methyl.

Derivative 32: 2-(N-acetyl-p-methoxy-anilino) 1-p-methoxyphenyl imidazole (m.p. 130° C); $R_1$=$R_2$=p-methoxyphenyl; $R_3$=acetyl; $R_4$=$R_5$=H.

Derivative 33: 5-methyl-2-(N-methyl-benzylamino0 1-phenyl imidazole (m.p. 232° C) $R_1$=phenyl; $R_2$=benzyl, $R_3$=$R_5$=methyl, $R_4$=H.

Derivative 34: 2-(N-methyl benzylamino)-1-phenyl imidazole (m.p. 128° C) $R_1$=phenyl; $R_2$=benzyl; $R_3$=methyl; $R_4$=$R_5$=H.

Derivative 35: 1-p-chlorophenyl-2-pyrrolidino imidazole (m.p. 191° C) $R_1$=p-chlorophenyl; $NR_2R_3$=pyrrolidino; $R_4$=$R_5$=H.

Derivative 36: 1-o-chlorophenyl-2-pyrrolidino imidazole (m.p. 165° C) $R_1$=o-chlorophenyl; $NR_2R_3$=pyrrolidino; $R_4$=$R_5$=H.

Derivative 37: 1-allyl-5-methyl-2-pyrrolidino imidazole (m.p. 142° C) $R_1$=allyl, $NR_2R_3$=pyrrolidino, $R_3$=$R_4$=H; $R_5$=methyl.

Derivative 38: 1-p-methoxyphenyl-5-methyl-2-pyrrolidino imidazole (m.p. 165° C) $R_1$=p-methoxyphenyl; $NR_2R_3$=pyrrolidino; $R_4$=H; $R_5$=methyl.

Derivative 39: 5-methyl-1-phenyl-2-[p-4-tolylpiperazino]imidazole (m.p. 183° C); $R_1$=phenyl; $NR_2R_3$=p-4-tolyl-piperazine; $R_4$=H; $R_5$=methyl.

Derivative 40: 2-(N-dichloroacetyl-p-chloroanilino)-p-1-chlorophenyl imidazole (m.p. 137° C); $R_4$=$R_5$=H; $R_1$=chlorophenyl; $R_2$=chlorophenyl; $R_3$=dichloroacetyl.

Derivative 41: 1-(β-phenethyl)-5-methyl-2-pyrrolidino imidazole (M.p. 159°–160° C) $R_1$=phenethyl, $NR_2R_3$=pyrrolidino; $R_4$=H; $R_5$=methyl.

Derivative 42: 1-β-phenethyl-2-pyrrolidino imidazole (m.p. > 260° C); $R_1$=phenethyl, $NR_2R_3$=pyrrolidino; $R_4$=$R_5$=H.

Derivtive 43: 1-allyl-2-pyrrolidino imidazole (m.p. 139° C) $R_1$=allyl; $NR_2R_3$=pyrrolidino; $R_4$=$R_5$=H.

Derivative 44: 1-p-hydroxyphenyl-5-methyl-2-pyrrolidino imidazole (m.p. > 250° C) $R_1$=p-hydroxyphenyl; $NR_2R_3$=pyrrolidino; $R_4$=H; $R_5$=$CH_3$.

Derivative 45: 2-(2,6-dichloro-anilino)-5-methyl 1-propargyl imidazole (m.p. 249°–251° C). $R_1$=propargyl; $NR_2R_3$2,6-dichloro-anilino; $R_4$=H; $R_5$=$CH_3$.

Derivative 46: 2-(2-chloro-anilino)-5-methyl-1-propargyl imidazole (m.p. 264°–266° C); $R_1$=propargyl; $NR_2R_3$=2-chloro-anilino; $R_4$=H; $R_5$=$CH_3$.

Derivative 47: 2-azepino-5-methyl-1-phenyl imidazole (m.p. 142° C); $R_1$=phenyl; $NR_2R_3$=azepino; $R_4$=H; $R_5$=$CH_3$.

Derivative 48: 5-methyl-2-pyrrolidino-1-(3-trifluoromethyl-phenyl) imidazole (m.p. 126° C); $R_1$=3-trifluoromethylphenyl; $NR_2R_3$=pyrrolidino; $R_4$=H; $R_5$=$CH_3$.

Derivative 49: 5-methyl-1-(3-methylmercaptophenyl)-2-pyrrolidino imidazole (m.p. 181° C) $R_1$=3-methyl-mercaptophenyl; $NR_2R_3$=pyrrolidino; $R_4$=H; $R_5$=$CH_3$.

Derivative 50: N-cyclohexyl, N-2-methylamino 5-methyl 1-phenyl imidazole (m.p. 142° C) $R_1$=phenyl; $NR_2R_3$=N,N-cyclohexylmethylamino; $R_4$=H; $R_5$=$CH_3$.

Derivative 51: 2-(p-4-chlorophenyl-piperazino) 1-phenyl imidazole (m.p. 183°–184° C); $R_1$=phenyl; $NR_2R_3$=4-p-chlorophenyl-piperazino; $R_4$=H; $R_5$=H.

Derivative 52: 2-(p-chloro-4-phenyl-piperazino) 5-methyl 1-phenyl imidazole (m.p. 212° C) $R_1$=phenyl; $NR_2R_3$=4-p-chlorophenyl-piperazino; $R_4$=H; $R_5$=$CH_3$.

Derivative 53: 2-(4-o-chlorophenyl-piperazino)-5-methyl-1-phenyl-imidazole (m.p. 120° C) $R_1$=phenyl; $N(R_2R_3)$=4-o-chlorophenyl-piperazino; $R_4$=4; $R_5$=$CH_3$.

The results of the pharmacological and pharamcological tests, which are reported hereinafter, demonstrate the interesting activities of the derivatives of the invention, particularly their psychostimulant and anti-inflammatory activities.

The invention therefore has as its object a medicament with, in particular, psychostimulant and anti-inflammatory activity, characterised in that it contains, as active principle, a derivative of formula I or an acid addition salt, or a pharmaceutically acceptable quaternary ammonium derivative of said derivative.

I TOXICOLOGICAL STUDY

This study demonstrated the good tolerance of the derivatives of the invention. As an indication, the $LD_{50}$/24 hours/kg of body weight, calculated according to the method of Miller and Tainter, for the intravenous route, in mice, is 50 mg for derivative 1, 78 mg for derivative 2, 100 mg for derivative 3, 52 mg for derivative 6, 85 mg for derivative 8, 50 mg for derivative 10, 73 mg for derivative 11, 57.5 mg for derivative 14, 65 mg for derivative 16, 51 mg for derivative 17, 24 mg for derivative 19, 40 mg for derivative 23, 90 mg for derivative 25, and 90 mg for derivative 26.

The tests showed that, throughout the tests for acute, chronic, subchronic or retarded toxicity, the derivatives of the invention caused no local or general reactions and no disturbances whatever, in the test animals, in the biological checks which were carried out at regular intervals.

II PHARMACOLOGICAL STUDY

This study was concerned with psychostimulant activity on the one hand and anti-inflammatory activity on the other hand.

1. Psychostimulant activity a. Study of behavior

The activity of the derivatives of the invention is studied in male mice, according to the technique of Samuel Irwin (Ph.D Animal and clinical Pharmacologic Technics in Drug Evaluation). The product being tested is administered by oral route in doses of 30 mg/kg. The animals' behavior is carefully observed for 4 hours from the administration of the product and the various physiological parameters are measured.

The stimulant activity, for all the derivatives of formula I, occurs as a distinct increase in the spontaneous activity and cries of the animals, their mobility, and also as an increase in their temperature and cardiac rate and respiratory frequency.

b. Antagonistic activity with regard to barbiturates (BOISSIER:l'Encephale, 1961, 50, 4, 340–359, and REVOL, Act. Pharmaceut. 1961, No. 10).

This test, carried out on 2 batches of mice, confirms that a normally hypnogenic dose of barbiturate is no longer sufficient to cause sleep if it is administered after a derivative of the invention.

The control batch A thus is given a 20 mg dose of barbiturate by intraperitoneal route. The test batch B is additionally given, orally, a 30 mg/kg dose of the derivative to be tested.

Then the number of animals asleep, the time taken to fall asleep and the period of sleep are determined, in the 2 batches of mice.

It is noted, as the average results given hereinafter show, that, for derivatives 3, 4 and 9, for example, the psychostimulant activity of the derivatives of the invention antagonizes the hypnotic effect of the barbiturate.

|  | % mice that fall asleep | Average time taken to fall asleep | Average length of sleep |
|---|---|---|---|
| Control mice | 100 | 11 minutes | 71 minutes |
| Treated mice | 5 | 27 minutes | 35 minutes | c. Antagonistic activity with regard to chloral hydrate

When administered to mice 30 minutes before an intraperitoneal injection of 300 mg/kg of chloral, the derivatives of the invention, for example derivatives 20, 27, 29 and 33, in a dose of 30 mg/kg, considerably reduce the number of animals that fall asleep and substantially reduce the length of their sleep.

Moreover, the derivatives of the invention inhibit hyperthermia, which is provoked in the oxotremorine test in mice, and cause a distinct anti-reserpinic activity in rats.

2. Anti-inflammatory activity

This activity was studied using 2 methods:

a. Generalized ovalbumen oedema method

The rat is simultaneously given an intraperitoneal injection of 1 ml of ovalbumen and 0.5 ml of a 1 part per 1000 aqueous solution of Evans blue.

Also, the animals in the treated batch are given 50 mg per os of the derivative to be tested, one hour before and at the same time as the ovalbumen. The intensity of the phenomenon thus caused is given a mark from 1 to 5, depending on the progression of the inflammatory syndrome. In this way, the average oedematous intensity is determined, with regard to the controls.

The percentages for derivatives 23 and 31, for example, were 59 and 53% respectively in the 2nd hour and 66 and 58% in the 3rd hour.

b. Method using localized oedema provoked by carrageenin

A 1% carrageenin solution (0.1 ml) is injected into the metatarsal flexors of the right hind paw of the rat at 0 hours.

The animals in the treated batch are also given, by oral route, 50 mg/kg of the derivative to be tested, one hour before, then at the same time as the injection of the phlogogenic agent, then one hour and 2½ hours after, respectively. The measurements, which are taken with a Roch micrometer at 0 hours, 1 hour, 2 hours, 3 hours and 5 hours after administration of the carrageenin, make it possible to determine the percentage of anti-inflammatory activity, as a function of the time, with regard to the control batch. The results show that, for derivatives 3 and 25, the respective percentages are 35 and 46% in the 1st hour, 42 and 49% in the 2nd hour, 47 and 55% in the 3rd hour and 58 and 60% in the 5th hour.

The toxicological and pharmacological studies which have been described above demonstrated the good tolerance and the interesting psycho-stimulant and anti-inflammatory properties of the derivatives of the invention.

The medicaments of the invention may, for oral administration, be in the form of tablets, coated tablets, capsules, syrup or drops. They may also be in the form of suppositories, for rectal administration, and injectable solutions, for parenteral administration.

Each individual dose of 0.05 to 2 g advantageously contains 0.025 to 0.500 g of active principle, while the dosage to be administered per 24 hours may vary from 0.025 g to 1 g of active principle.

Since the medicaments of the invention possess considerable psychostimulant properties, in both the pharmacological and clinical fields, while they lack the harmful side effects which are common in this category of products, they may be of great service in therapy. In fact, they stimulate mental activity and promote thought, have a favorable effect on moods and reduce agitation and anxiety, and, moreover, restore integration of sensory perceptions.

They are suitable for administration in cases of mental strain, nervous and psychic asthenia, educational backwardness, psychosomatic fatigue, minor neurotic or reaction depression, mental and behavioral disturbance in old age.

Moreover, they demonstrate a powerful anti-inflammatory activity on different stages of inflammation, without causing any intolerances of the digestive type.

They further have a favorable effect on chronic inflammatory rheumatism, degenerative rheumatism, abarticular infections, acute gout, functional re-education, inflammatory conditions of a urological-pulmonary origin, otorhinolaryngology, traumatology, and in post-operative treatment in plastic and cosmetic surgery.

What I claim is:

1. A compound of the formula:

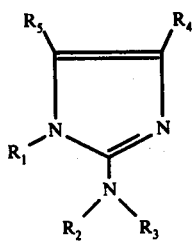

wherein $R_1$ is selected from phenyl and phenyl monosubstituted with a member selected from halogen, lower alkyl, lower alkoxy, diloweralkylamino, lower alkoxycarbonyl, lower alkylthio, trifluoromethyl, nitro and cyano, $R_4$ is selected from hydrogen and lower alkyl, $R_5$ is selected from hydrogen and methyl, and $R_2$ and $R_3$ form, together with the nitrogen atom to which they are bonded a saturated heterocycle having 4 to 8 ring members, among which one is the nitrogen atom and the others are carbon atoms, and their pharmaceutically acceptable salts.

2. The compound of claim 1, wherein the heterocycle is pyrrolidino.

3. 5-methyl-1-phenyl-2-pyrrolidino-imidazole and its pharmaceutically acceptable salts.

4. Psychostimulant composition in individual dose of 0.05 to 2 g comprising a pharmaceutically acceptable carrier and from 0.025 to 0.500 g of a compound having the formula

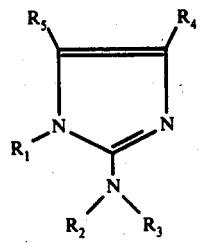

wherein $R_1$ is selected from phenyl and phenyl monosubstituted with a member selected from halogen, lower alkyl, lower alkoxy, diloweralkylamino, lower alkoxycarbonyl, lower-alkylthio, trifluoromethyl, nitro and cyano, $R_4$ is selected from hydrogen and lower alkyl, $R_5$ is selected from hydrogen and methyl, and $R_2$ and $R_3$ form, together with the nitrogen atom to which they are bonded a saturated heterocycle having 4 to 8 ring members, among which one is the nitrogen atom and the others are carbon atoms, and their pharamaceutically acceptable salts.

* * * * *